United States Patent [19]

Mills

[11] 4,298,855
[45] Nov. 3, 1981

[54] CONDUCTIVE POLYMER FILM HUMIDITY SENSOR

[75] Inventor: Frank S. Mills, Minneapolis, Minn.

[73] Assignee: Honeywell Inc., Minneapolis, Minn.

[21] Appl. No.: 181,507

[22] Filed: Aug. 26, 1980

[51] Int. Cl.³ ............................................. H01L 7/00
[52] U.S. Cl. ...................................... 338/35; 338/195; 338/309; 422/98
[58] Field of Search ................. 338/35, 195, 307–309; 219/121 L, 121 LM, 219 LH, 121 LJ; 340/602; 324/65 R; 73/27 R, 336, 336.5; 23/232 E; 422/98, 88; 357/75

[56] References Cited

U.S. PATENT DOCUMENTS

| 2,638,783 | 5/1953 | Rittner et al. | 338/35 |
| 2,714,149 | 7/1955 | Craig et al. | 338/35 |
| 3,295,088 | 12/1966 | Smith | 338/35 |
| 3,458,845 | 6/1972 | Thoma | 338/35 |
| 3,671,913 | 6/1972 | Mamiya et al. | 338/35 |
| 3,699,649 | 10/1972 | McWilliams | 219/121 L |
| 3,821,093 | 6/1974 | Carron et al. | 73/336.5 |
| 3,848,218 | 11/1974 | Wakabayashi et al. | 338/35 |
| 3,891,958 | 6/1975 | Wakabayashi | 338/35 |
| 3,914,982 | 10/1975 | Zanetti | 73/336.5 X |
| 3,943,557 | 3/1976 | Frazee | 357/75 |
| 3,983,527 | 9/1976 | Ohsato et al. | 338/35 |
| 4,016,308 | 4/1977 | Frazee | 338/35 X |
| 4,025,892 | 5/1977 | Pompei et al. | 338/35 |
| 4,224,565 | 4/1980 | Sosniak et al. | 338/35 X |

Primary Examiner—C. L. Albritton
Attorney, Agent, or Firm—Alfred N. Feldman

[57] ABSTRACT

A humidity sensor utilizes a conductive polymer film that normally exhibits a variable resistance characteristic. The polymer film also exhibits a humidity responsive function that can be utilized while the temperature responsive function is balanced out. The device is capable of a high level of calibration by the use of laser trimming of the conductive polymer film resistors.

9 Claims, 2 Drawing Figures

CONDUCTIVE POLYMER FILM HUMIDITY SENSOR

BACKGROUND OF THE INVENTION

The measurement and control of humidity has been a very difficult and relatively expensive function. While there are many materials that are sensitive to humidity, the reliable and repeatable application of these elements for control of humidity has been found to be difficult. Most simple and inexpensive humidity responsive devices and materials yield a humidity measurement which is unreliable and which generally is not overly accurate. Simple acting elements to sense humidity have been used for many years to provide indicators for the percent of relative humidity. More accurate humidity sensing and/or control has relied on relatively expensive humidity sensing elements and electronics. Since most humidity indicating systems are temperature responsive, some type of temperature compensating has had to be applied to the typical humidity control in order to obtain any reasonable level of accuracy.

As a result of the difficulty of measuring and controlling humidity accurately, there are a large number of humidity sensitive indicators and control systems, but cost and accuracy problems plague most of these units.

DESCRIPTION OF THE INVENTION

The present humidity sensor results from the utilization of a characteristic of a conductive polymer film. Conductive polymer films have been used for many years to form resistors in electronic devices through the use of hybrid technology. Conductive polymer films that contain particles of carbon as a resistance element are deposited or silk screened onto a nonconductive substrate. Many times this substrate mounts additional components for use in electronic circuits. It has been found that conductive polymer films that are used for the production of hybrid resistors tend to be humidity responsive and this characteristic generally has been considered undesirable. Some work has been directed to make conductive polymer films that are stable, that is, that do not vary in resistance with humidity. This humidity sensitive characteristic of the conductive polymer film is recognized as an advantage in the present invention, rather than as a disadvantage.

Since conductive polymer films are known to be sensitive to humidity, it was determined that this otherwise undesirable characteristic could be used for the production of a simple, inexpensive, and accurate humidity sensor. The present invention utilizes four conductive polymer film resistors that are deposited on a single substrate that is not affected by humidity. The resistors are connected in a series circuit that in turn is connected into a bridge configuration. Three of the four resistors are sealed into a hermetically tight chamber so that varying humidity around the substrate does not affect those three resistors. One of the resistors is left exposed to the atmosphere and responds to a change in humidity. Since all four resistors are in close proximity to one another, are of the same material, and are deposited on a single substrate, the changes in temperature that affect one of the resistors affects all of the resistors. With the resistors used in a bridge configuration, the change of temperature can be balanced out and only the change in humidity of the one exposed resistor is measured. This change in humidity is then used to control any type of bridge responsive system.

In the present invention the accuracy of the resistors can be readily controlled by laser trimming the conductive polymer film through a glass or transparent window that forms one wall of the hermetically sealed chamber means.

DESCRIPTION OF THE PREFERRED EMBODIMENTS

Figure 1:
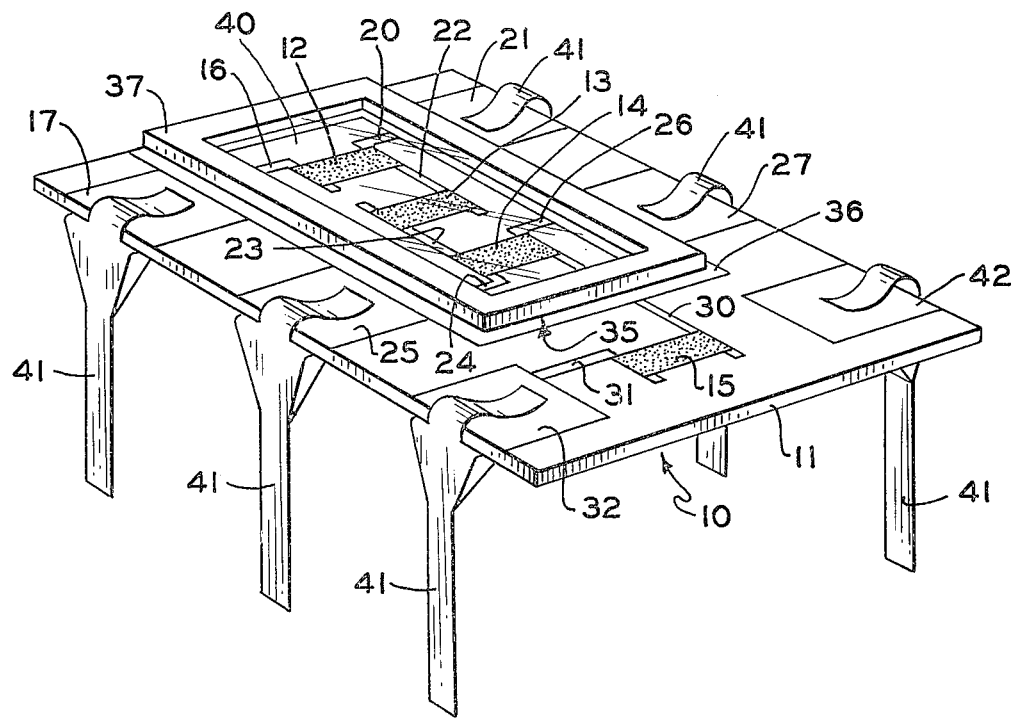
FIG. 1 is a pictorial view of a complete humidity sensor.

In FIG. 1 a pictorial view of a complete humidity sensor 10 is disclosed. The humidity sensor 10 utilizes a self-supporting insulating substrate member 11. The substrate member 11 should be of a material which is generally unaffected by humidity and which is an electrical insulating type material. An example of a material that is functionally practical for the self-supporting substrate means 11 is a substrate made of aluminum oxide. Many other types of materials, particularly materials in the ceramics family, would be suitable for this purpose.

Deposited on the substrate 11 are four electrical resistors 12, 13, 14, and 15. The electrical resistors 12, 13, 14, and 15 typically would be deposited on the substrate 11 by means of a screen printing process and the resistors would be made of a polymer film that incorporates carbon particles to form the conductive (or resistive) portions of the resistors 12, 13, 14, and 15. It has been found that carbon based polymer films used to form a resistive material tend to vary in resistivity with the amount of humidity in the atmosphere surrounding the film. As was pointed out earlier in the present specification, the humidity sensitive aspects have generally been considered a detriment and the polymer film resistance material has been formulated to minimize the humidity effect. In the present device, the polymer film resistance material takes advantage of the humidity sensitive characteristic of the film. The total chemistry of this type of film is not material to the present invention. Polymer materials that the film resistors are printed from can vary widely in their composition, and the more humidity sensitive the material is, the more desirable the particular polymer film resistance material may be.

The resistor 12 is connected to a conductive path 16 that in turn is connected to a conductive area 17. The path 16 and the area 17 are screened onto the substrate 11 in a conventional hybrid technology process. The resistor 12 is further connected to a conductor 20 and an area 21, as well as by a conductor 22 to the resistor 13. The resistor 13 then in turn is connected at 23 to the resistor 14. The resistor 14 is connected by a conductor 24 to a conductive area 25. The resistor 14, at its other side, is connected by a conductor 26 to a conductive area 27. This same side of resistor 14 is connected by a further conductor 30 to one side of the resistor 15. The resistor 15 then is connected by a conductor 31 to a conductive area 32.

It will be noted that a continuous resistor means can be traced which includes all four of the resistors 12, 13, 14, and 15. A continuous or series electrical circuit can be traced from the area 17, the conductor 16, the resistor 12, the conductor 22, the resistor 13, the conductor 23, the resistor 14, the conductor 30, the resistor 15, the conductor 31, and the area 32. In each case, the resistors 12, 13, 14, and 15 further have connection means to individual conductive areas to form a plurality of terminals for the humidity sensor so that the humidity sensor can be connected in a bridge circuit where the four resistors form the four legs of a conventional Wheatstone type of bridge. This arrangement will become clear in connection with the arrangement disclosed in FIG. 2.

In order to make the humidity sensor disclosed in FIG. 1 functional, a hermetically impervious housng means is generally disclosed at 35. The hermetically impervious housing means 35 encloses the resistors 12, 13, and 14 by encircling the resistors with a dielectric layer or ring 36 that mounts in a solder type seal a member 37 that has a window area 40 over the resistors 12, 13, and 14. The window area 40 in the center of the member 37 typically would be a glass window that is hermetically sealed through the means of a dielectric layer to the substrate 11. The window 40 is used for laser trimming of the resistors 12, 13, and 14 as will be explained in connection with FIG. 2. The window 14 typically would be made of a form of glass that has a thermal coefficient of expansion that is compatible with the balance of the structure. The only requirements of the window 40 is that it be transparent for the laser trimming process that will be described in connection with FIG. 2.

In the disclosure of FIG. 1, the humidity sensor 10 is completed by the addition of a plurality of soldered mounted contact members 41 that attach to each of the conductive areas 17, 25, 32, 21, 27, and a blank conductive area 42 so that six mounting terminals are provided. These mounting terminals are used to conveniently mount the humidity sensor of FIG. 1 into a printed circuit board or into a socket, as the case may dictate. It should be noted that the use of the terminals 41 is not essential to the present invention, but that the conductive areas to which the terminals 41 connect could be adapted to be mounted in any other convenient manner such as by lead wires, etc.

Figure 2:
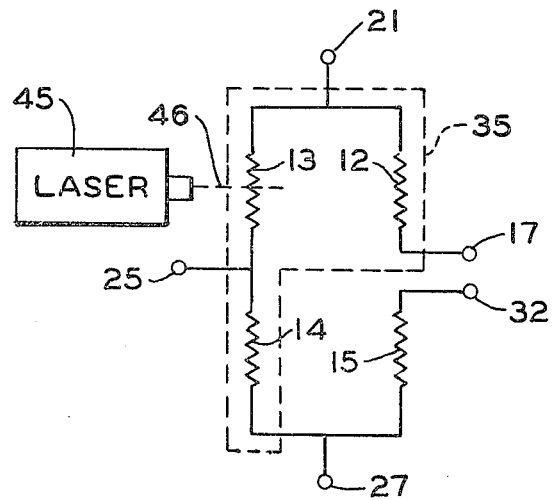
FIG. 2 is a schematic representation of the conductive polymer film resistors that make up the humidity sensor.

Before an explanation of how the device functions, it is believed desirable to complete an explanation of the structure and calibration of the unit. In FIG. 2 the four resistors 12, 13, 14, and 15 have been disclosed along with the conductive areas which are connected to the ends of each of the resistors. It will be noted in FIG. 2 that the conductive area or terminal 17 connects through the resistor 12 and then to the resistor 13 at the terminal 21. The resistor 13 is connected to resistor 14 which is connected in common with the terminal or conductive area 25. The resistor 14 is then connected to the conductive area or terminal 27 and to one side of the resistor 15. The resistor 15 is connected to the terminal 32. A circuit between the terminals 17 and 32 forms a series circuit or electric circuit means in which all of the resistors are interconnected. With the arrangement as disclosed it is possible to measure the value of each of the resistors 12, 13, 14, and 15 by connection to the external terminal 17, 21, 25, 27, and 32. This is done for a very specific reason. The resistors are provided in an electric circuit means that is capable of measurement so that a laser trimming technique can be used to trim the resistors for calibration purposes through the window 40. A laser 45 has been disclosed with a beam 46 that is directed through the window 40 to the resistor 13. By measuring the resistance between the terminals 21 and 25 it is possible to accurately trim the resistor 13 with the laser 45 for calibration purposes. Each of the resistors is capable of being trimmed in a similar manner. Typically, 17 and 32 are shorted and only one resistor is selected by computer to be trimmed for voltage calibration in a bridge configuration. The hermetically impervious housing means 35 has been shown as a dotted line around the resistors 12, 13, and 14. The resistor 15 is left exposed to the ambient humidity so that its humidity can be allowed to change with the ambient while the resistors 12, 13, and 14 are kept stable at a single dew point level in the hermetically impervious housing means 35.

Since all of the resistors 12, 13, 14, and 15 are mounted in close proximity to one another and are on a single substrate 11, any temperature change which would affect these resistors can be balanced out by the bridge configuration shown. As such the humidity sensor 10 does not allow the polymer film resistances, which will change resistance with temperature, to affect the sensing of humidity to which the resistor 15 is exposed.

With the present simple device, a normally unwanted effect of humidity on a polymer film resistor is taken advantage of. The device is capable of being produced at a reasonable expense and provides a humidity sensor that is substantially immune to variations in temperature while measuring the humidity of an ambient to which the entire device is exposed. The present device has been disclosed in one single embodiment incorporating standard materials and structure. The concept of the present invention could be varied by the physical structure and types of materials used. The applicant wishes to be limited in the scope of his invention, solely by the scope of the appended claims.

The embodiments of the invention in which an exclusive property or right is claimed are defined as follows:

1. A humidity sensor utilizing a conductive polymer film, including: self-supporting insulating substrate means which is unaffected by humidity; polymer film resistor means deposited upon said substrate means with said resistor means including a plurality of resistors; conductive connection means deposited upon said substrate means to interconnect said resistors in electric circuit means; said conductive connection means further including conductive areas connected to said resistors to form a plurality of terminals which are adapted to be used to connect said resistors in a bridge; hermetically impervious housing means mounted on and sealed to said substrate to form hermetically sealed chamber means; said chamber means enclosing all but one of said resistors in said chamber means; and said one unenclosed resistor being exposed to an ambient atmosphere whose humidity is to be measured by said unenclosed resistor varying in resistance value with the ambient humidity for comparison with a fixed dew point present in said sealed chamber means.

2. A humidity sensor as described in claim 1 wherein said conductive connection means interconnects said resistors in series electric circuit means.

3. A humidity sensor as described in claim 2 wherein said housing means includes a transparent window with said housing means mounted on said substrate means to form said chamber means with said window facilitating the trimming of said polymer film resistor means through said window by means of a laser.

4. A humidity sensor as described in claim 3 wherein said transparent window includes a flat glass member; and said flat glass member is mounted generally parallel to said substrate means.

5. A humidity sensor as described in claim 4 wherein said plurality of terminals are adjacent an edge of said substrate means to facilitate the mounting of said humidity sensor.

6. A humidity sensor as described in claim 5 wherein said humidity sensor further includes terminal extensions attached to said plurality of terminals adjacent said edge of said substrate means and electrically connected thereto to provide mounting means for said humidity sensor.

7. A humidity sensor as described in claim 4 wherein said insulating substrate means has a generally uniform thermal characteristic; and said resistors are deposited in close proximity to each other to maintain said resistors at substantially the same temperature when said humidity sensor is exposed to said ambient humidity.

8. A humidity sensor as described in claim 7 wherein said plurality of terminals are adjacent an edge of said substrate means to facilitate mounting of said humidity sensor.

9. A humidity sensor as described in claim 8 wherein said humidity sensor further includes terminal extensions attached to said plurality of terminals adjacent said edge of said substrate means and electrically connected thereto to provide mounting means for said humidity sensor.

* * * * *